United States Patent
Sandberg et al.

(10) Patent No.: US 9,944,677 B2
(45) Date of Patent: Apr. 17, 2018

(54) SELECTIVE INHIBITOR OF ANGIOTENSIN II

(71) Applicant: GEORGETOWN UNIVERSITY, Washington, DC (US)

(72) Inventors: Kathryn Sandberg, Silver Spring, MD (US); Jun Liu, Germantown, MD (US); Hong Ji, Chevy Chase, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/776,601

(22) PCT Filed: Mar. 12, 2014

(86) PCT No.: PCT/US2014/024755
§ 371 (c)(1),
(2) Date: Sep. 14, 2015

(87) PCT Pub. No.: WO2014/151011
PCT Pub. Date: Sep. 25, 2014

(65) Prior Publication Data
US 2016/0024151 A1    Jan. 28, 2016

Related U.S. Application Data

(60) Provisional application No. 61/793,107, filed on Mar. 15, 2013.

(51) Int. Cl.
| | | |
|---|---|---|
| *A61K 38/00* | (2006.01) | |
| *A61K 38/08* | (2006.01) | |
| *C07K 7/06* | (2006.01) | |
| *C07K 14/72* | (2006.01) | |

(52) U.S. Cl.
CPC .............. *C07K 7/06* (2013.01); *C07K 14/72* (2013.01); *A61K 38/00* (2013.01)

(58) Field of Classification Search
CPC ........ A61K 38/00; A61K 38/08; C07K 14/72; C07K 7/06
USPC .......................................... 514/16.3; 530/329
See application file for complete search history.

(56) References Cited

U.S. PATENT DOCUMENTS

| | | | |
|---|---|---|---|
| 7,101,963 B2 * | 9/2006 | Griffais ................ | C07K 14/295 424/184.1 |
| 2003/0148324 A1 | 8/2003 | Bingen et al. | |
| 2004/0006218 A1 | 1/2004 | Griffais et al. | |
| 2006/0123505 A1 | 6/2006 | Kikuchi et al. | |
| 2007/0053927 A1 | 3/2007 | Griffais et al. | |
| 2009/0274701 A1 | 11/2009 | Griffais et al. | |
| 2012/0246748 A1 | 9/2012 | Guo et al. | |

OTHER PUBLICATIONS

M0JZU9 from UniProt., pp. 1-4. Integrated into UniProtKB on Apr. 3, 2013.*
G4QJ13 from UniProt., pp. 1-8. Integrated into UniProtKB on Dec. 14, 2011.*
International Search Report dated Jul. 18, 2014 issued in PCT application (No. PCT/US2014/024755).
Written Opinion dated Jul. 18, 2014 issued in PCT application (No. PCT/US2014/024755).
F0K1Z1, UniProtKB/TrEMBL accession No. F0KIZ1_LACD2, May 3, 2011[online]. [Retrieved on Jun. 21, 2014]. Retrieved from the internet <URL: http://www.uniprot.org/uniprot/F0K1Z1.1xt?version=14> Entire document.
Q1GAF1, UniProtKB/TrEMBL accession No. Q1GAF1_LACDA, Jan. 9, 2013 [online] [Retrieved on Jun. 21, 2014]. Retrieved from the internet <URL: http://www.uniprot.org/uniprot/Q1GAF1.txt?version=54>.
J9GGY0, UniProtKB/TrEMBL accession No. J9GGY0_9ZZZZ, Oct. 31, 2012 [online] [Retrieved on Jun. 21, 2014]. Retrieved from the internet <URL: http://www.uniprot.org/uniprot/J9GGY0.txt?version=1>.
J0L8X0, UniProtKB/TrEMBL accession No. J0L8X0_9BACT, Nov. 28, 2012 [online] [Retrieved on Jun. 21, 2014]. Retrieved from the internet <URL: http://www.uniprot.org/uniprot/J0L8X0.txt?version=3>.
G6EUJ3, UniProtKB/TrEMBL accession No. G6EUJ3_LACDE, Nov. 28, 2012 [online] [Retrieved on Jun. 21, 2014]. Retrieved from the internet <URL: http://www.uniprot.org/uniprot/G6EUJ3.bct?version=7>.
Liu et al., "Small peptide PEP7 can decease Angiotensin II (Ang II) induced function through MAPK signaling pathway." *The FASEB Journal*. Apr. 2013, vol. 27, Meeting abstract 936.1. Entire abstract.
Liu et al., "Selective inhibition of angiotensin receptor signaling through Erk1/2 pathway by a novel peptide." *Am J Physiol Regul Integr Comp Physiol.*, Feb. 2014, 306: R619-R626.

* cited by examiner

*Primary Examiner* — Julie Ha
(74) *Attorney, Agent, or Firm* — Womble Bond Dickinson (US) LLP (57) ABSTRACT

Peptides and peptide analogs that selectively inhibit angiotensin II are described. Additionally, a method for making and using the peptides and peptide analogs are also described.

3 Claims, 6 Drawing Sheets

SEQUENCE LISTING

```
<160> NUMBER OF SEQ ID NOS: 4

<210> SEQ ID NO 1
<211> LENGTH: 7
<212> TYPE: PRT
<213> ORGANISM: Rattus rattus

<400> SEQUENCE: 1

Met Ala Gly Ile Leu Ser Gly
1               5

<210> SEQ ID NO 2
<211> LENGTH: 7
<212> TYPE: PRT
<213> ORGANISM: Homo sapiens

<400> SEQUENCE: 2

Met Ala Gly Phe Leu Ser Glu
1               5

<210> SEQ ID NO 3
<211> LENGTH: 21
<212> TYPE: DNA
<213> ORGANISM: Rattus rattus

<400> SEQUENCE: 3
atggcgggca ttctgagcgg c                                         21

<210> SEQ ID NO 4
<211> LENGTH: 21
<212> TYPE: DNA
<213> ORGANISM: Homo sapiens

<400> SEQUENCE: 4
atggcgggct ttctgagcga a                                         21
```

SELECTIVE INHIBITOR OF ANGIOTENSIN II

STATEMENT REGARDING FEDERALLY SPONSORED RESEARCH OR DEVELOPMENT

This invention was made with government support under Grant R01 HL57502 awarded by the National Heart, Lung, and Blood Institute. The government has certain rights in inventions disclosed herein.

SEQUENCE LISTING

The instant application contains a Sequence Listing, which has been submitted in ASCII format via EFS-Web and is hereby incorporated by reference in its entirety. Said ASCII copy, created on 10 Jul. 2016, is named SUBS_SEQL.txt and is 8 kB in size.

TECHNICAL FIELD OF THE INVENTION

The invention relates generally to peptides and peptide mimetics that selectively inhibit angiotensin II, as well as methods for making and using the same.

BACKGROUND OF THE INVENTION

Hypertension and associated diseases including stroke, atherosclerosis and chronic kidney disease remain the number one cause of death throughout the world. In the United States, more than fifty percent of hypertensive patients do not have their blood pressure under good control; most patients need more than one medication to achieve their target blood pressure. Suboptimal blood pressure control is in part due to poor patience compliance because of the adverse side effects (e.g., dizziness, headache, cough, sexual dysfunction) associated with the widely prescribed angiotensin converting enzyme inhibitors (ACEi) and angiotensin receptor blockers (ARBs).

Angiotensin II (Ang II) inhibitors are in the top ten global therapeutic classes of pharmaceuticals. In 2008, global sales of Ang II inhibitors exceeded $22 billion and sales are expected to reach $30 billion by 2015. Accordingly, there would be great commercial demand for novel Ang II inhibitors/receptor antagonists that have a therapeutic profile that is distinct from ACEi and ARBs; such novel Ang II inhibitors/receptor antagonists could exhibit synergistic effects and/or reduce off-target adverse events (e.g., sexual dysfunction) through lowered dosages.

BRIEF SUMMARY OF THE INVENTION

The present invention relates to a selective inhibitor of angiotensin II, a peptide named PEP7, as well as polynucleotides encoding PEP7, vectors and cells expressing PEP7 polynucleotides, and PEP7 peptide mimetics.

The present invention also relates to methods of treating hypertension and inhibiting angiotensin II in a subject using PEP7 peptides and peptide mimetics, polynucleotides, vectors and cells of the present invention. In particular embodiments, the subject is an animal. In other embodiments, the subject is a human.

DETAILED DESCRIPTION OF THE INVENTION

PEP7 Peptides and Peptide Mimetics

As used herein, the term "peptide" and plural variants refer to a compound made up of a single chain of amino acids joined by peptide bonds. PEP7 peptides may comprise naturally occurring amino acids, synthetic amino acids, genetically encoded amino acids, non-genetically encoded amino acids, and combinations thereof. Polypeptides may include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative synthetic amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Methods of chemically synthesizing peptides comprising any of the foregoing types of amino acids are known to one of ordinary skill in the art (e.g., solid-phase peptide synthesis).

Exemplary PEP7 peptides include MAGILSG (SEQ ID NO: 1) and MAGFLSE (SEQ ID NO: 2).

Isolated PEP7 peptides may be purified and characterized using a variety of standard techniques that are known to the skilled artisan (see e.g., Schröder et al., *The Peptides*, 1965, Academic Press, New York; Bodanszky, *Principles of Peptide Synthesis*, 2nd rev. ed. 1993, Springer-Verlag, Berlin/New York; Ausubel (ed.), *Short Protocols in Molecular Biology*, 3rd ed., 1995, Wiley, New York).

PEP7 Nucleic Acids

As used herein, the terms "nucleic acid", "polynucleotide", "polynucleotide molecule", "polynucleotide sequence" and plural variants are used interchangeably to refer to a wide variety of molecules, including single strand and double strand DNA and RNA molecules, cDNA sequences, genomic DNA sequences of exons and introns, chemically synthesized DNA and RNA sequences, and sense strands and corresponding antisense strands. Polynucleotides of the invention may also comprise known analogs of natural nucleotides that have similar properties as the corresponding natural nucleic acid.

Exemplary PEP7 polynucleotides of the invention include ATGGCGGGCATTCTGAGCGGC (SEQ ID NO: 3), ATGGCGGGCTTTCTGAGCGAA (SEQ ID NO: 4) and other degenerate DNA and RNA sequences encoding PEP7 peptides contemplated by the present invention.

Nucleic acids of the invention also comprise nucleic acids complementary to SEQ ID NOs: 1 and subsequences and elongated sequences of SEQ ID NOs: 1 and complementary sequences thereof. Complementary sequences are two nucleotide sequences that comprise anti-parallel nucleotide sequences capable of pairing with one another upon formation of hydrogen bonds between base pairs. Like other polynucleotides in accordance with the present invention, complementary sequences maybe substantially similar to one another as described previously. A particular example of a complementary nucleic acid segment is an antisense oligonucleotide.

An elongated sequence is one in which nucleotides (or other analogous molecules) are added to a nucleic acid sequence. For example, a polymerase (e.g., a DNA polymerase) may add sequences at the 3' terminus of the nucleic acid molecule. In addition, the nucleotide sequence may be combined with other DNA sequences, such as promoters, promoter regions, enhancers, polyadenylation signals, introns, additional restriction enzyme sites, multiple cloning sites, and other coding segments. Thus, the present invention also provides vectors comprising the disclosed nucleic acids, including vectors for recombinant expression, wherein a nucleic acid of the invention is operatively linked to a functional promoter. When operatively linked to a nucleic acid, a promoter is in functional combination with the nucleic acid such that the transcription of the nucleic acid is controlled and regulated by the promoter region. Vectors refer to nucleic acids capable of replication in a host cell, such as plasmids, cosmids, and viral vectors.

A subsequence is a sequence of nucleic acids that comprises a part of a longer nucleic acid sequence. An exemplary subsequence is a probe or a primer. Conditions under which a nucleic acid probe or primer will typically hybridize to its target sequence but to no other sequences when that sequence is present in a complex nucleic acid mixture (e.g., total cellular DNA or RNA) are stringent in nature. In the context of nucleic acid hybridization experiments such as Southern and Northern blot analyses, stringent hybridization conditions and stringent hybridization wash conditions are both sequence- and environment-dependent. An extensive guide to the hybridization of nucleic acids is found in Tijssen, *Laboratory Techniques in Biochemistry and Molecular Biology-Hybridization with Nucleic Acid Probes*, part I chapter 2, Elsevier, New York (1993).

Polynucleotides of the present invention may be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions is also known in the art (see e.g., Sambrook et al. (eds.) *Molecular Cloning: A Laboratory Manual*, 1989, Cold Spring Harbor Laboratory Press, Cold Spring Harbor, N.Y.; Silhavy et al., *Experiments with Gene Fusions*, 1984, Cold Spring Harbor Laboratory Press, Cold Spring Harbor, N.Y.; Glover & Hames, *DNA Cloning: A Practical Approach*, 2nd ed., 1995, IRL Press at Oxford University Press, Oxford/New York; Ausubel (ed.) *Short Protocols in Molecular Biology*, 3rd ed., 1995, Wiley, New York).

PEP7 Expression Systems

An expression system refers to a host cell comprising a heterologous nucleic acid and the protein encoded by the heterologous nucleic acid. For example, a heterologous expression system may comprise a host cell transfected with a construct comprising a PEP7 nucleic acid encoding a protein operatively linked to a promoter, or a cell line produced by introduction of PEP7 nucleic acids into a host cell genome. The expression system may further comprise one or more additional heterologous nucleic acids relevant to PEP7 function, such as targets of PEP7 transcriptional activation or repression activity. These additional nucleic acids may be expressed as a single construct or multiple constructs.

A construct for expressing a PEP7 protein may include a vector sequence and a PEP7 nucleotide sequence, wherein the PEP7 nucleotide sequence is operatively linked to a promoter sequence. A construct for recombinant PEP7 expression may also comprise transcription termination signals and sequences required for proper translation of the nucleotide sequence. Constructs may also contain a 'signal sequence' or 'leader sequence' to facilitate co-translational or post-translational transport of the peptide of interest to certain intracellular structures such as the endoplasmic reticulum or Golgi apparatus. Constructs can also contain 5' and 3' untranslated regions. A 3' untranslated region is a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. A 5' untranslated region is a polynucleotide located upstream of a coding sequence. Preparation of an expression construct, including addition of translation and termination signal sequences, is known to one skilled in the art.

The promoter may be any polynucleotide sequence that shows transcriptional activity in the host cell. The promoter may be native or analogous, or foreign or heterologous, to the host cell and/or to the DNA sequence of the invention. Where the promoter is native or endogenous to the host cell, it is intended that the promoter is found in the cell into which the promoter is introduced. Where the promoter is foreign or heterologous to the DNA sequence of the invention, the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley et al., *Nucleic Acids Res.*, 15:2343-61 (1987). Also, the location of the promoter relative to the transcription start may be optimized (see e.g., Roberts et al., *Proc. Natl. Acad. Sci. USA,* 76:760-4 (1979)). Many suitable promoters for use in human cell lines are well known in the art. The promoter may include, or be modified to include, one or more enhancer elements to thereby provide for higher levels of transcription. Where appropriate, the vector and PEP7 sequences may be optimized for increased expression in the transformed host cell. That is, the sequences can be synthesized using host cell-preferred codons for improving expression, or may be synthesized using codons at a host-preferred codon usage frequency.

Host Cells

Host cells are cells into which a heterologous nucleic acid molecule of the invention may be introduced. A host cell line may be chosen which modulates the expression of the recombinant sequence, or modifies and processes the gene product in a specific manner. For example, different host cells have characteristic and specific mechanisms for the translational and post-translational processing and modification (e.g., glycosylation, phosphorylation of proteins). Appropriate cell lines or host cells may be chosen to ensure the desired modification and processing of the foreign protein expressed.

The present invention further encompasses recombinant expression of a PEP7 protein in a stable cell line. Methods for generating a stable cell line following transformation of a heterologous construct into a host cell are known in the art (see e.g., Joyner, *Gene Targeting: A Practical Approach*, 1993, Oxford University Press, Oxford/New York). Thus, transformed cells and tissues are understood to encompass not only the end product of a transformation process, but also transgenic progeny or propagated forms thereof.

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

PEP7

In the rat, two distinct mRNA transcripts are synthesized from the angiotensin 1a receptor (AT1aR) gene by alternative splicing. One of the two transcripts contains exons 1, 2 and 3 (E1,2,3), while the other contains exons 1 and 3 (E1,3). In the E1,2,3 transcript, the 5' leader sequence (5'LS) is comprised of exons 1, 2 and 52 by of exon 3; in the E1,3 transcript, the 5'LS includes exon 1 and 52 by of exon 3. In both transcripts, the entire coding region and the 3' untranslated region (3'UTR) exist within exon 3. Therefore, the two AT1aR mRNA transcripts that differ in the 5'LS length encode the same identical AT1aR protein. The presence of two variants of the AT1aR mRNA suggests that alternative splicing of the 5'LS is involved in post-transcriptional regulation of AT1aR gene expression. Despite the identical amino acid sequence of the AT1aR in both transcripts, E1,2,3 mRNA is translated less efficiently than the E1,3 mRNA. Furthermore, the E1,2,3 mRNA is associated with lower AT1aR densities with less efficient signal transduction compared to the E1,3 mRNA variant.

Figure 1:
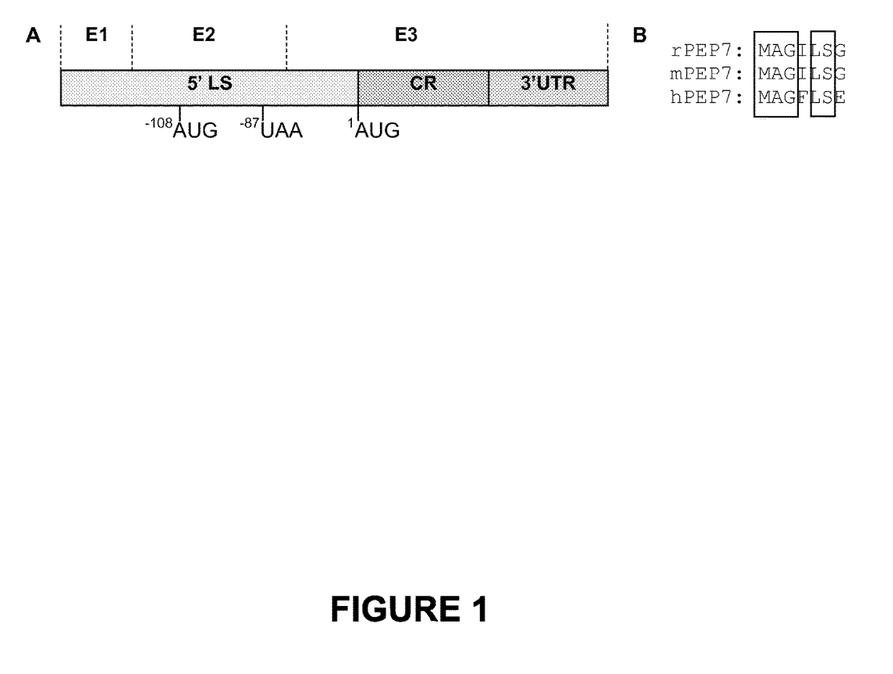
FIG. 1 shows a schematic of the rat AT mRNA. A) The rat AT1aR mRNA contains 3 exons; B) PEP7 (rPEP7; MAGILSG (SEQ ID NO: 1)) is identical to mouse PEP7 (mPEP7) and homologous to human PEP7 (hPEP7; MAGFLSE (SEQ ID NO: 2)).

Sequence analysis of E2 revealed a short open reading frame that encodes a seven amino acid peptide (PEP7) from −108AUG to −87TAA, which is in frame with the AT1aR coding region (see FIG. 1A). The amino acid sequence of PEP7 is markedly conserved in rats and mice and humans (see FIG. 1B); the sequence of PEP7 in rat and mouse is MAGILSG (SEQ ID NO: 1), whereas the sequence of the human homolog is MAGFLSE (SEQ ID NO: 2) (see FIG. 1B).

Example 2

PEP7 Inhibits Translation and AT1aR Binding

Figure 2:
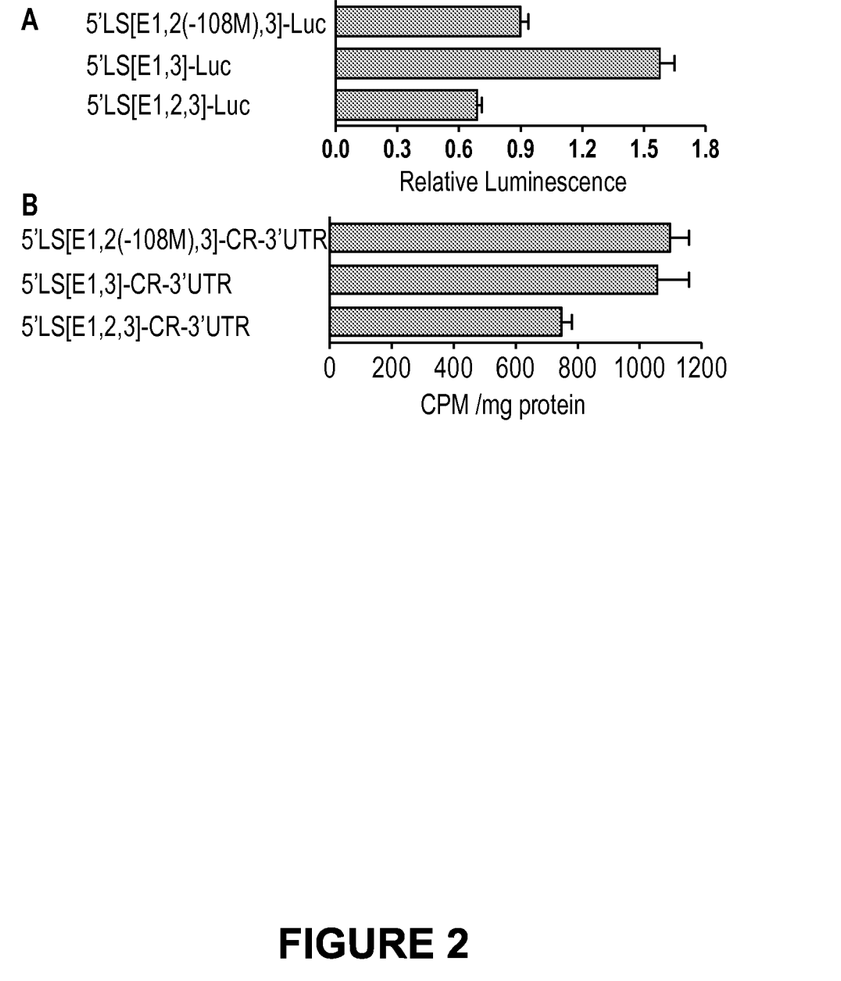
FIG. 2 shows how disruption of the PEP7 start codon releases the E2 repression of A) luciferase activity & B) $AT_1R$ binding.

To investigate the function of the short open reading frame encoding PEP7, the 5'LS portions of the E1,3 and E1,2,3 transcripts as well as an E1,2,3 transcript in which the AUG start codon was disrupted by site-directed mutagenesis at position −108 (E1,2(−108M),3) were all placed upstream of luciferase (Luc) generating 5'LS [E1,3]-Luc, 5'LS[E1,2,3]-Luc and 5'LS[E1,2(−108M),3]-Luc constructs. Then, Luc reporter assays were conducted in transiently transfected HEK293 cells. The presence of exon 2 inhibited Luc activity by 60% while disruption of the short open reading frame start codon attenuated this inhibition (see FIG. 2A). When this short opening reading frame start codon was disrupted in the full length E1,2,3 transcript (5'LS[E1,2(−108M),3-CR-3'UTR) and then expressed in HEK293 cells, radioligand binding studies demonstrated that AT1aR binding increased by 1.5 fold compared to the non-mutated transcript (5'LS[E1,2,3]-CR-3'UTR), suggesting PEP7 inhibits AT1aR translation and receptor binding (see FIG. 2B).

Example 3

PEP7 Inhibits Ang II Induction of Erk1/2

Figure 3:
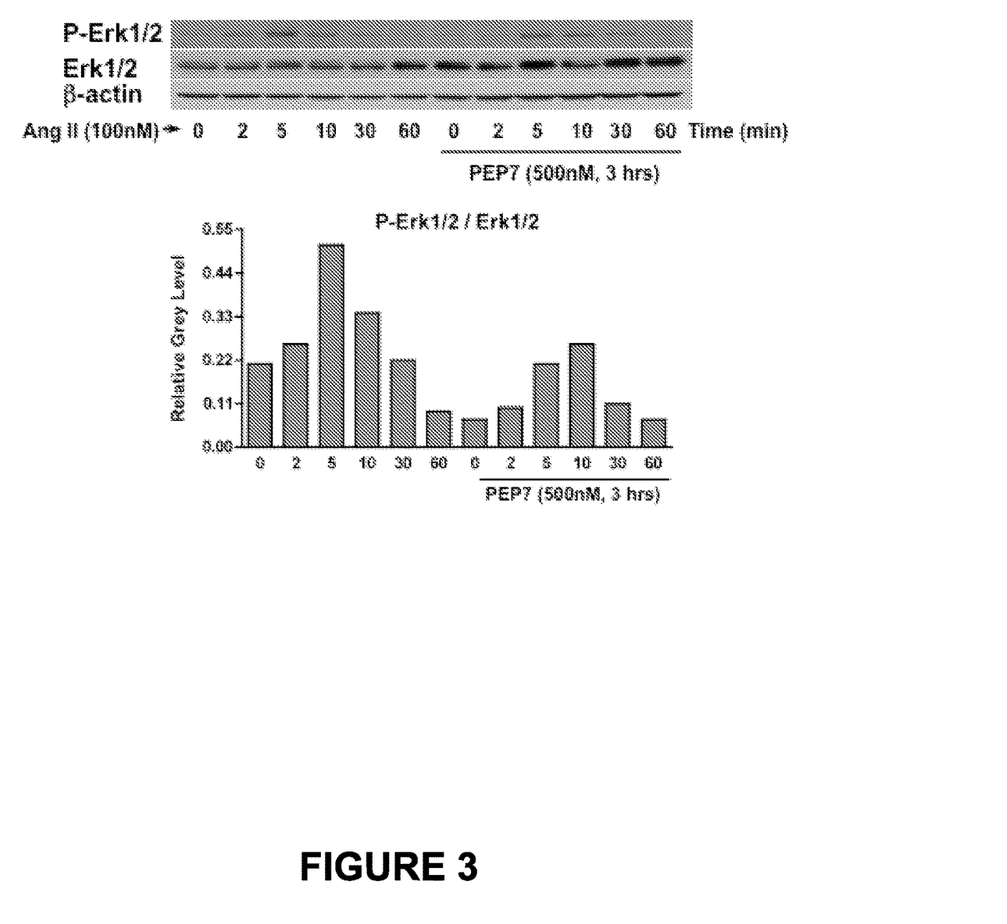
FIG. 3 shows how PEP7 inhibits Ang II-induced pERK1/2 expression. The gel is representative of triplicates.

The $AT_1R$ is one of the most versatile members of the G protein-coupled receptor family. Upon Ang II binding, the $AT_{1a}R$ mediates signal transduction through multiple signaling pathways including $IP_3$, Erk1/2, and NFκB. To determine the effects of PEP7 on $AT_{1a}R$ signaling, HEK293 cells were transfected with the full length $AT_{1a}R$. 48 hours after transfection, 100 nM Ang II rapidly increased the expression of phosphoErk1/2 (pErk1/2) with maximum expression occurring after 5 minutes. Pre-incubation of the cells with 500 nM PEP7 markedly attenuated this induction by Ang II (see FIG. 3).

Example 4

PEP7 Attenuation of Arterial Pressure

Figure 4:
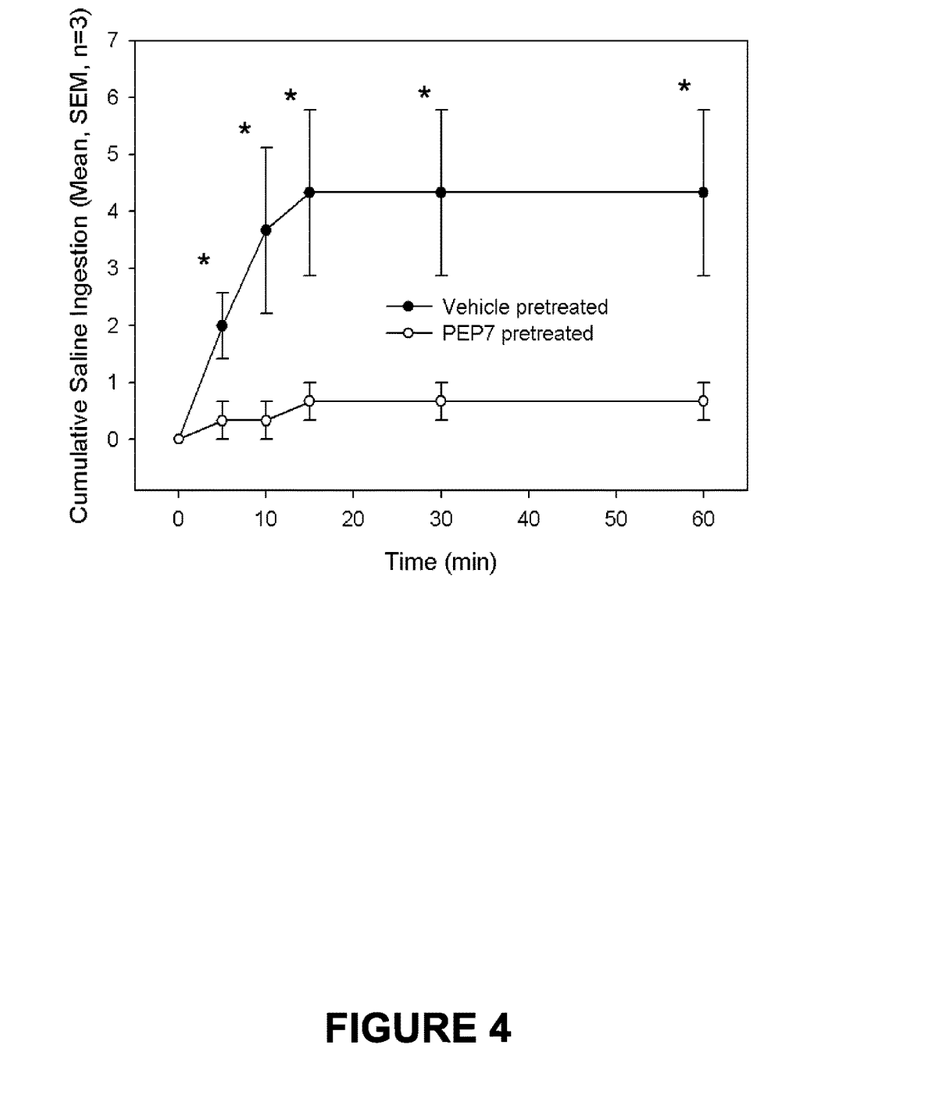
FIG. 4 shows how PEP7 attenuates arterial blood pressure.

The effect of PEP7 on blood pressure and heart rate was determined. Six New Zealand white rabbits (weighing 4 kg each) were instrumented with radiotransmitters and stainless steel i.c.v. cannulas. After recovery from surgery, the rabbits were injected i.c.v. with 100 ng PEP7 or a 100 ng of a scrambled version of PEP7 (sPEP7) >while recording systolic blood pressure (SBP), diastolic blood pressure (DBP) and heart rate. PEP7 significantly attenuated basal systolic and diastolic blood pressure whereas the scrambled peptide had minimal effects (see FIG. 4 and Table 1).

TABLE 1

|  | Baseline | Max Effect | Change |
|---|---|---|---|
| PEP7 | | | |
| SBP (mm Hg) | 94 | 85 | −9 |
| DBP (mm Hg) | 70 | 62 | −8 |
| MAP (mm Hg) | 79 | 69 | −10 |
| sPEP7 | | | |
| SBP (mm Hg) | 95 | 92 | −3 |
| DBP (mm Hg) | 69 | 67 | −2 |
| MAP (mm Hg) | 78 | 74 | −4 |

Example 5

Figure 5:
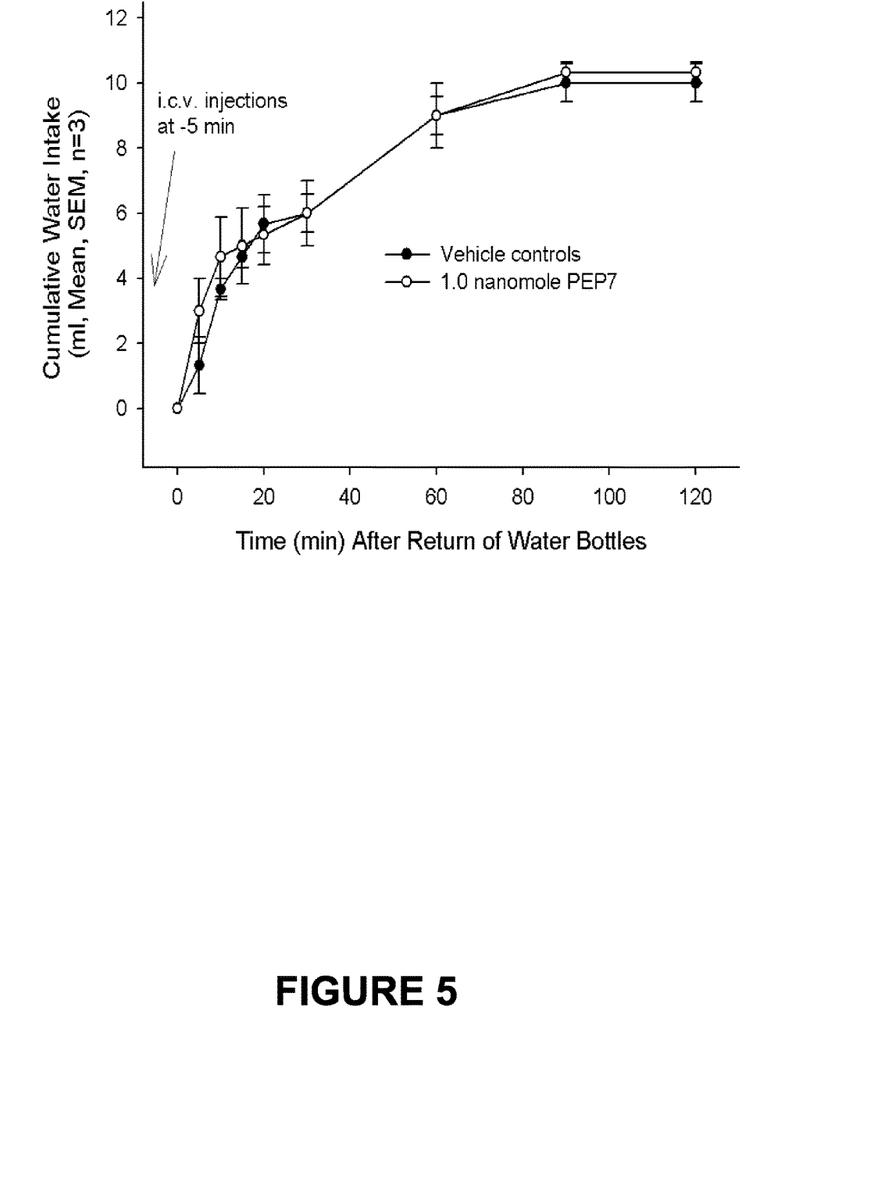
FIG. 5 shows how PEP7 inhibits Ang II-induced sodium appetite. The data are expressed as the mean±SEM; n=3; *p<0.05 vs. PEP7 treatment.
Figure 6:
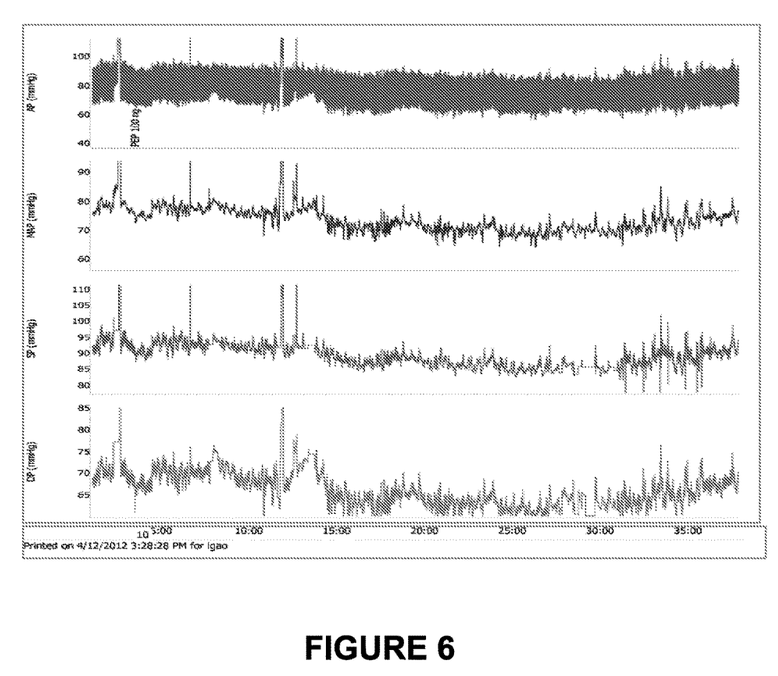
FIG. 6 shows that PEP7 has no effect on water deprivation-induced drinking behavior. The data are expressed as the mean±SEM; n=3.

PEP7 Attenuation of Salt Appetite 1 nM PEP7 markedly decreased i.c.v. Ang II-induced saline ingestion in rats (without affecting i.c.v. Ang II-induced water intake (see FIG. 5). Moreover, i.c.v. PEP7 failed to inhibit dehydration-induced water intake (see FIG. 6). In addition, PEP7 did not have an effect on behavioral arousal, locomotion and grooming behavior. This suggests PEP7 selectively inhibits $AT_1R$ signaling via the ERK1/2 pathway since Ang II-induced sodium appetite is Erk1/2 dependent while Ang II-induced drinking behavior is not.

The disclosure of every patent, patent application, and publication cited herein is hereby incorporated herein by reference in its entirety. While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A selective inhibitor of angiotensin II consisting essentially of amino acids having the sequence MAGFLSE (SEQ ID NO: 2).

2. The selective inhibitor of angiotensin II of claim 1, wherein glycine is replaced with sarcosine.

3. A method of treating hypertension in a subject comprising administering a composition comprising the selective inhibitor of angiotensin II of claim 1 to the subject.

* * * * *

UNITED STATES PATENT AND TRADEMARK OFFICE
CERTIFICATE OF CORRECTION

PATENT NO. : 9,944,677 B2
APPLICATION NO. : 14/776601
DATED : April 17, 2018
INVENTOR(S) : Kathryn Sandberg et al.

It is certified that error appears in the above-identified patent and that said Letters Patent is hereby corrected as shown below:

In the Specification

The heading and paragraph at Column 1, Lines 4-10 should read as follows:
--STATEMENT REGARDING FEDERALLY SPONSORED RESEARCH OR DEVELOPMENT
This invention was made with government support under grant number HL057502 awarded by the National Institutes of Health. The government has certain rights in the invention.--

Signed and Sealed this
Seventh Day of November, 2023

Katherine Kelly Vidal
*Director of the United States Patent and Trademark Office*